United States Patent [19]

Böger et al.

[11] 4,386,102
[45] May 31, 1983

[54] PHENYL-N-(CYANOALKYLSULFENYL)-N-METHYLCARBAMATES AND THE USE THEREOF IN PEST CONTROL

[75] Inventors: Manfred Böger, Weil am Rhein, Fed. Rep. of Germany; Jözef Drabek, Oberwil, Switzerland

[73] Assignee: Ciba-Geigy Corporation, Ardsley, N.Y.

[21] Appl. No.: 327,879

[22] Filed: Dec. 7, 1981

[30] Foreign Application Priority Data

Dec. 17, 1980 [CH] Switzerland ................. 9305/80

[51] Int. Cl.³ ............... A01N 47/22; C07C 125/067
[52] U.S. Cl. ......................... 424/304; 260/465 D
[58] Field of Search ............... 260/465 D; 424/304

[56] References Cited

U.S. PATENT DOCUMENTS

| | | | |
|---|---|---|---|
| 3,847,951 | 12/1974 | Kohn et al. | 260/346.2 |
| 3,897,483 | 7/1975 | Bernady et al. | 260/488 R |
| 4,058,549 | 11/1977 | D'Silva | 260/465.4 |
| 4,179,514 | 12/1979 | D'Silva | 424/277 |
| 4,305,957 | 12/1981 | Drabek et al. | 424/285 |

FOREIGN PATENT DOCUMENTS 25014 11/1981 European Pat. Off. .

*Primary Examiner*—Dolph H. Torrence
*Attorney, Agent, or Firm*—Frederick H. Rabin

[57] ABSTRACT

The invention relates to phenyl-N-(cyanoalkylsulfenyl)-N-methylcarbamates of the formula

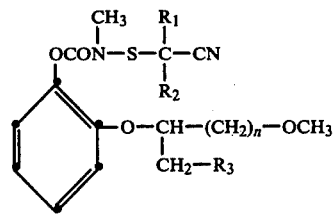

wherein each of $R_1$ and $R_2$ is methyl, or both together with the nitrogen atom to which they are attached are a cyclopentyl radical, $R_3$ is hydrogen or chlorine, and n is 0 or 1.

The invention relates to the production of these compounds and to their use in pest control.

7 Claims, No Drawings

PHENYL-N-(CYANOALKYLSULFENYL)-N-METHYLCARBAMATES AND THE USE THEREOF IN PEST CONTROL

The present invention relates to phenyl-N-(cyanoalkylsulfenyl)-N-methylcarbamates, to the production thereof, and to the use thereof in pest control.

The phenyl-N-(cyanoalkylsulfenyl)-N-methylcarbamates of this invention have the formula

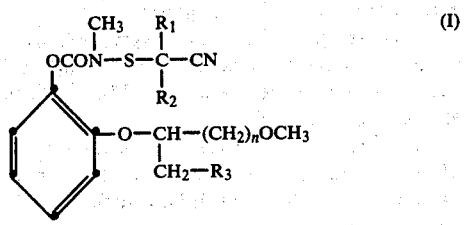

wherein each of $R_1$ and $R_2$ are methyl, or both together with the carbon atom to which they are attached are a cyclopentyl radical, $R_3$ is hydrogen or chlorine, and n is 0 or 1.

The compounds of formula I can be obtained by methods which are known per se, for example as follows:

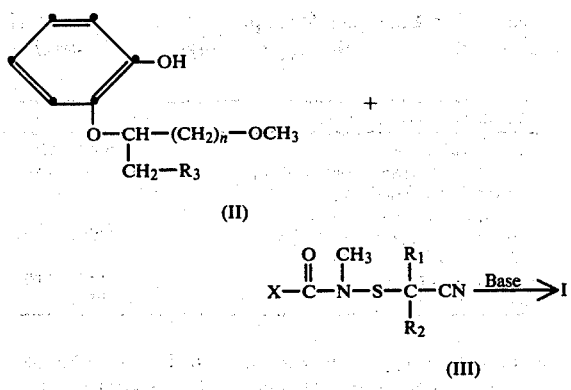

In formulae II and III above, $R_1$, $R_2$, $R_3$ and n are as defined for formula I and X in formula III is a halogen atom, in particular a fluorine or chlorine atom.

The process is carried out at a reaction temperature from $-50°$ to $+130°$ C., preferably from $-10°$ to $+100°$ C., under normal or slightly elevated pressure and in the presence of a solvent or diluent which is inert to the reactants.

Suitable bases for this process are, in particular, tertiary amines such as trialkylamines, pyridines and dialkyl anilines, and also hydroxides, oxides, carbonates and bicarbonates of alkali metals and alkaline earth metals, as well as alkali metal alcoholates, e.g. potassium tert-butylate and sodium methylate.

Examples of suitable solvents or diluents are: ethers and ethereal compounds such as diethyl ether, diisopropyl ether, dioxane, tetrahydrofurane; aliphatic and aromatic hydrocarbons, especially benzene, toluene, and xylenes; and ketones such as acetone, methyl ethyl ketone and cyclohexanone.

The starting materials of the formula II and III are known or they can be obtained by methods analogous to known ones.

The compounds of formula I are suitable for controlling pests of animals and plants. These compounds also have fungicidal and plant regulating properties. In particular, the compounds of formula I are suitable for controlling insects, e.g. of the order Lepidoptera, Coleoptera, Homoptera, Heteroptera, Diptera, Acarina, Thysanoptera, Orthoptera, Anoplura, Siphonaptera, Mallophaga, Thysanura, Isoptera, Psocoptera and Hymenoptera, as well as mites and ticks of the order Acarina.

Most particularly, the compounds of formula I are suitable for controlling plant-destructive insects, especially plant-destructive feeding insects, in ornamentals and crops of useful plants, chiefly in cotton (e.g. against *Spodoptera littoralis* and *Heliothis virescens*) and in vegetables (e.g. against *Leptinotarsa decemlineata* and *Myzus persicae*).

In this connection, particular attention is drawn to the fact that the compounds of formula I have both a strongly pronounced systemic and contact action against sucking insects, especially against sucking insects of the order Homoptera and, most particularly, against insects of the Aphididae family (e.g. against *Aphis fabae, Aphis craccivora* and *Myzus persicae*), which can only be controlled with difficulty using known pesticides.

The compounds of formula I also have a very useful action against flies, e.g. *Musca domestica*, and mosquito larvae. In addition, they have a broad ovicidal and ovilarvicidal action. Furthermore, the compounds of formula I have a useful action against phytoparasitic nematodes as well as against ectoparasitic mites and ticks, e.g. of the families Ixodidae, Argasidae and Dermanyssidae.

The compounds of the formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. Like the nature of the compositions, the methods of application, such as spraying, atomising, dusting, scattering or pouring, are chosen in accordance with the intended objectives and the prevailing circumstances.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and contain a $C_8$–$C_{22}$alkyl radical which also includes the alkyl moiety of acyl radicals, e.g. the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ringwood, N.J., 1979.

The pesticidal formulations usually contain 0.1 to 99%, preferably 0.1 to 95%, of a compound of the formula I, 1 to 99.9% of a solid or liquid adjuvant, and 0 to 25%, preferably 0.1 to 25%, of a surfactant.

Whereas commercial products are preferably formulated as concentrates, the end user will normally employ dilute formulations.

The formulations can also contain further additives such as stabilisers, antifoams, viscosity regulators, binders, adhesives, as well as fertilisers, in order to produce special effects.

FORMULATION EXAMPLES

Formulation Examples for liquid active ingredients of the formula I (throughout, percentages are by weight)

| (1) Emulsifiable concentrates | (a) | (b) | (c) |
|---|---|---|---|
| active ingredient | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any required concentration can be produced from such concentrates by dilution with water.

| (2) Solutions | (a) | (b) | (c) | (d) |
|---|---|---|---|---|
| active ingredient | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20 | — | — |
| epoxidised coconut oil | — | — | 1% | 5% |
| petroleum distillate (boiling range 160-190°) | — | — | 94% | — |

These solutions are suitable for application in the form of microdrops.

| (3) Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (4) | Dusts | (a) | (b) |
|---|---|---|---|
| | active ingredient | 2% | 5% |
| | highly dispersed silicic acid | 1% | 5% |
| | talcum | 97% | — |
| | kaolin | — | 90% |

Ready-for-use dusts are obtained by intimately mixing the carriers with the active ingredient.

Formulation examples for solid active ingredients of the formula I (throughout, percentages are by weight)

| (5) | Wettable powders | (a) | (b) |
|---|---|---|---|
| | active ingredient | 20% | 60% |
| | sodium lignosulfonate | 5% | 5% |
| | sodium laurylsulfate | 3% | — |
| | sodium diisobutylnaphthalenesulfonate | — | 6% |
| | oxtylphenol polyethylene glycol ether (7-8 moles of ethylene oxide) | — | 2% |
| | highly dispersed silicic acid | 5% | 27% |
| | kaolin | 67% | — |

The active ingredient is thoroughly mixed with the adjuvants and the mixtures is thoroughly ground in a suitable mill, affording wettable powders which can be diluted with water to give suspensions of the desired concentration.

| (6) | Emulsifiable concentrate | |
|---|---|---|
| | active ingredient | 10% |
| | octylphenol polyethylene glycol ether (4-5 moles of ethylene oxide) | 3% |
| | calcium dodecylbenzenesulfonate | 3% |
| | castor oil polyglycol ether (36 moles of ethylene oxide) | 4% |
| | cyclohexanone | 30% |
| | xylene mixture | 50% |

Emulsions of any required concentration can be obtained from this concentrate by dilution with water.

| (7) | Dusts | (a) | (b) |
|---|---|---|---|
| | active ingredient | 5% | 8% |
| | talcum | 95% | — |
| | kaolin | — | 92% |

Ready-for-use dusts are obtained by mixing the active ingredient with the carriers, and grinding the mixture in a suitable mill.

| (8) | Extruder granulate | |
|---|---|---|
| | active ingredient | 10% |
| | sodium lignosulfonate | 2% |
| | carboxymethylcellulose | 1% |
| | kaolin | 87% |

The active ingredient is mixed and ground with the adjuvants, and the mixture is subsequently moistened with water. The mixture is extruded and then dried in a stream of air.

| (9) | Coated granulate | |
|---|---|---|
| | active ingredient | 3% |
| | polyethylene glycol 200 | 3% |
| | kaolin | 94% |

The finely ground active ingredient is uniformly applied, in a mixer, to the kaolin moistened with polyethylene glycol. Non-dusty coated granulates are obtained in this manner.

| (10) | Suspension concentrate | |
|---|---|---|
| | active ingredient | 40% |
| | ethylene glycol | 10% |
| | nonylphenol polyethylene glycol ether (15 moles of ethylene oxide) | 6% |
| | sodium lignosulfonate | 10% |
| | carboxymethylcellulose | 1% |
| | 37% aqueous formaldehyde solution | 0.2% |
| | silicone oil in the form of a 75% aqueous emulsion | 0.8% |
| | water | 32% |

The finely ground active ingredient is intimately mixed with the adjuvants, giving a suspension concentrate from which suspensions of any desired concentration can be obtained by dilution with water.

Example 1

Production of N-(2-isobutyrocyanosulfenyl)-2-(2-chloro-1-methoxyethoxy)phenyl-N-methylcarbamate With stirring, 6.6 g of triethylamine and then, at 25° C., (2-fluorocarbonyl-4-cyano-4-methyl)-2-aza-4-sulfa-pentane are added dropwise to a solution of 10.6 g of 2-(2-chloro-1-methoxyethoxy)phenol in 120 ml of toluene. The reaction mixture is stirred for 16 hours at 50° C. The cold toluene solution is washed with three 50 ml portions of water, dried over sodium sulfate and concentrated. The crude product is chromatographed over silica gel with methylene chloride as eluant, affording the compound of the formula

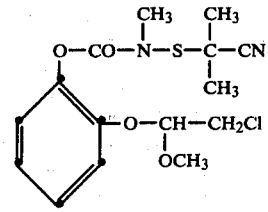

with a refractive index of $n_D^{20°} = 1.5301$.

The following compounds are also prepared in analogous manner:

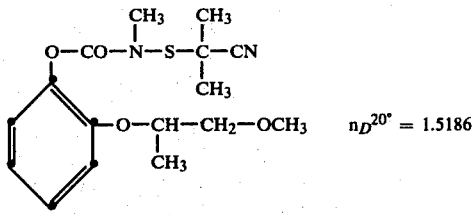

$n_D^{20°} = 1.5186$

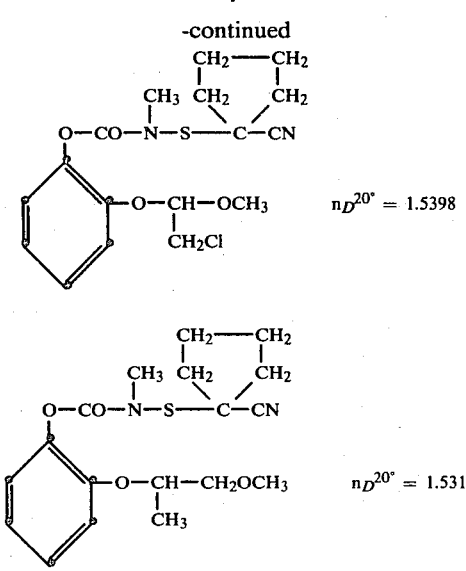

BIOLOGICAL EXAMPLES

Example 2

Insecticidal stomach poison action against *Anthonomus grandis*

Cotton plants are sprayed with a solution containing 50, 100, 200 or 400 ppm of the compound to be tested. After the coating has dried, the plants are populated with larvae of the species *Anthonomus grandis* (adults). Two plants are used for each test compound and test species. A mortality count is made after 2, 4, 24 and 48 hours. The test is carried out at 24° C. and 60% relative humidity.

The compounds of Example 1 act against insects of the species *Anthonomus grandis* as shown in the table.

Example 3

Insecticidal contact action against *Myzus persicae*

Before the start of the test, bean plants (*Vicia faba*) reared in water are each populated with about 200 insects of the species *Myzus persicae*. The treated plants are sprayed 3 days later dripping wet from a distance of 30 cm with a solution containg 10 or 1 ppm of the compound to be tested. Two plants are used for each test compound at its given concentration and a mortality count is made after a further 24 hours.

Within the above concentration limits, the compounds of Example 1 act against insects of the species *Myzus persicae*, as shown in the table.

Example 4

Systemic insecticidal action against *Aphis craccivora*

Bean plants which have grown roots are transplanted into pots containing 600 ccm of soil and then 50 ml of a solution containing 25 ppm, 5 ppm or 1 ppm of the compound to be tested are poured direct onto the soil. After 24 hours the parts of the plants above the soil are populated with lice of the species *Aphis craccivora* and a plastic cylinder is then slipped over the plants and tied at the bottom to protect the lice from any possible contact with the test substance either directly or via the gas phase. A mortality count is made 24 and 48 hours respectively after the start of the test. Two plants, each in a separate pot, are used for each test substance at its given concentration. The test is carried out at 25° C. and 70% relative humidity.

The compounds of Example 1 act against insects of the species *Aphis craccivora* as shown in the table.

Biological Test Results

The results of the tests carried out in the foregoing Examples are reported in the table, using the following rating to indicate the percentage kill of the pests:

A: 70–100% kill at a concentration of 1 ppm
B: 70–100% kill at a concentration of 5 ppm
C: 70–100% kill at a concentration of 10 ppm
D: 70–100% kill at a concentration of 25 ppm
E: 70–100% kill at a concentration of 50 ppm
F: 70–100% kill at a concentration of 100 ppm
G: 70–100% kill at a concentration of 200 ppm
H: 70–100% kill at a concentration of 400 ppm

| Compound | Action against | | |
|---|---|---|---|
| | *Anthonomus grandis* | *Myzus persicae* | *Aphis craccivora* |
| (structure 1) | F | A | A |
| (structure 2) | F | A | B |
| (structure 3) | E | C | B |
| (structure 4) | F | C | B |

What is claimed is:

1. A phenyl-N-(cyanoalkylsulfenyl)-N-methylcarbamate of the formula

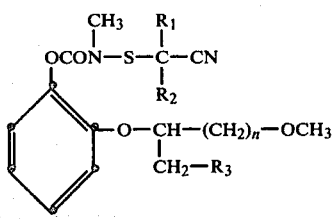

wherein each of $R_1$ and $R_2$ is methyl, or both together with the carbon atom to which they are attached form a cyclopentyl radical, $R_3$ is hydrogen or chlorine, and n is 0 or 1.

2. The compound according to claim 1 of the formula

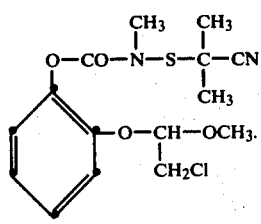

3. The compound according to claim 1 of the formula

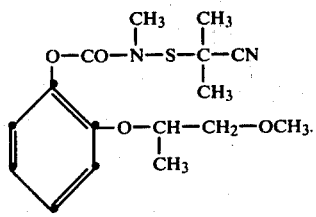

4. The compound according to claim 1 of the formula

5. The compound according to claim 1 of the formula

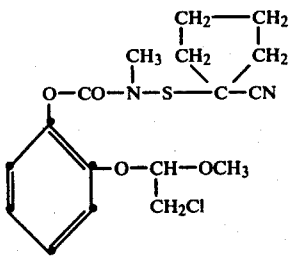

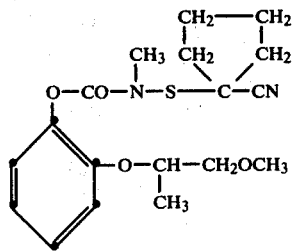

6. A method of controlling insects and acarids, which comprises applying to the locus thereof a pesticidally effective amount of a compound according to claim 1.

7. An insecticidal and acaricidal composition which comprises (1) as active component an insecticidally or acaricidally effective amount of a compound according to claim 1, and (2) a carrier.

* * * * *